United States Patent [19]

Kleiner et al.

[11] 4,060,681
[45] Nov. 29, 1977

[54] UNSATURATED ESTERS OF POLYFLUOROALKYLTHIOALCOHOLS

[75] Inventors: Eduard K. Kleiner, New York; Robert Ernest Arthur Dear, Mount Kisco, both of N.Y.

[73] Assignee: Ciba-Geigy Corporation, Ardsley, N.Y.

[21] Appl. No.: 657,140

[22] Filed: Feb. 11, 1976

[51] Int. Cl.$^2$ ............................................. C07G 69/54
[52] U.S. Cl. .............................. 560/222; 260/326.25; 560/195; 526/214; 526/321
[58] Field of Search ........................ 260/486 H, 485 F

[56] References Cited

U.S. PATENT DOCUMENTS

| 3,763,116 | 10/1973 | Kleiner et al. | 260/485 F |
| 3,906,049 | 9/1975 | Hager et al. | 260/485 F |

FOREIGN PATENT DOCUMENTS

| 2,255,672 | 6/1973 | Germany | 260/485 F |

*Primary Examiner*—Paul J. Killos
*Attorney, Agent, or Firm*—Karl F. Jorda; Edward McC. Roberts; Prabodh I. Almaula

[57] ABSTRACT

This invention relates to novel acrylates, methacrylates, fumarates, maleates, citraconates, mesaconates, itaconates, and aconitates of the following structure:

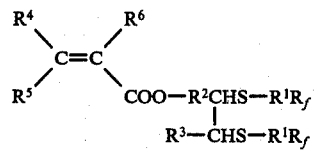

where
$R^1$, $R^2$ are each $C_nH_{2n}$, where $n$ is 1 to 12 and may be straight chain or branched;
$R^3$ is hydrogen or $C_nH_{2n+1}$, where $n$ is 1 to 12 and may be straight chain or branched;
$R^4$, $R^5$ and $R^6$ are hydrogen, methyl,

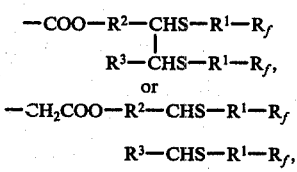

provided that at least one of $R^4$, $R^5$, and $R^6$ is hydrogen or methyl; $R_f$ is $C_pF_{2p+1}$ or $C_pF_{2p+1}OC_qF_{2q}$, where $p$ is 3 to 18 (preferably 6 to 12), $q$ is 2 to 8, and the perfluoroalkyl constituent may be branched or straight chain.

Addition polymers made from the above unsaturated esters are particularly useful for treating fabrics to make the fabric oil and water repellent.

14 Claims, No Drawings

UNSATURATED ESTERS OF POLYFLUOROALKYLTHIOALCOHOLS

This invention relates to novel acrylated, methacrylates, fumarates, maleates, citraconates, mesaconates, itaconates, and aconitates of the following structure:

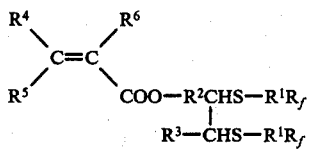

where $R^1$, $R^2$ are each $C_nH_{2n}$, where $n$ is 1 to 12 and may be straight chain or branched;

$R^3$ is hydrogen or $C_nH_{2n+1}$, where $n$ is 1 to 12 and may be straight chain or branched;

$R^4$, $R^5$ and $R^6$ are hydrogen, methyl,

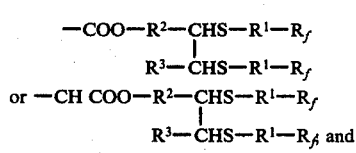

$R_f$ is $C_pF_{2p+1}$ or $C_pF_{2p+1}OC_qF_{2q}$, where $p$ is 3 to 18 preferably 6 to 12), $q$ is 2 to 8, and the perfluoroalkyl constituent may be branched or straight chain.

Polymers derived from monomers of Formula I have repeating units of the following structure:

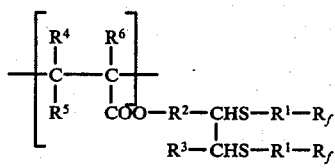

where $R^1$, $R^2$, $R^3$, $R^4$, $R^5$, $R^6$ and $R_f$ are as defined previously.

Monomers of Formula I are prepared by the reaction of the corresponding alcohols with $\alpha,\beta$-unsaturated acids of Formula III, or esters, anhydrides or acid chlorides thereof.

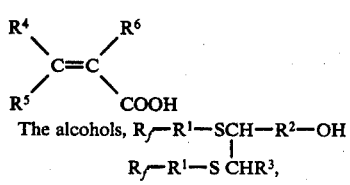

The alcohols, $R_f-R^1-SCH-R^2-OH$
              |
              $R_f-R^1-S\;CHR^3$, are disclosed in copending application Ser. No. 652,367 filed Jan. 26, 1976, Dear and Brace, which application is here incorporated by reference. The $\alpha,\beta$-unsaturated acids of Formula III, or their esters, anhydrides or acid chlorides are available commercially. These are, for example,

| Formula III $\alpha,\beta$ Unsaturated Acids | $R^4$ | $R^5$ | $R^6$ |
|---|---|---|---|
| Acrylic acid | -H | -H | -H |
| Methacrylic acid | -H | -H | -CH$_3$ |
| Fumaric acid | -COOH | -H | -H |
| Maleic acid | -H | -COOH | -H |
| Mesaconic acid | -COOH | -H | -CH$_3$ |
| Citranoic acid | -H | -COOH | -CH$_3$ |
| Itaconic acid | -H | -H | -CH$_2$COOH |
| cis Aconitic acid | -COOH | -H | -CH$_2$COOH |
| trans Aconitic acid | -H | -COOH | -CH$_2$COOH |

The novel esters of Formula I are obtained from the designated alcohols and the $\alpha,\beta$-unsaturated compounds of Formula III by well-known esterification or transesterification procedures. Many Formula III acids have high melting points and are poorly soluble in many common solvents, thus it is often preferable to use the acid chlorides, anhydrides or lower alkyl esters of the acids.

Polymerization of Perfluoroalkyl Monomers of Formula I

Polymers possessing soil repellent properties may be formed from $R_f$-monomers of Formula I. The polymers contemplated by this invention include homopolymers, copolymers with other ethylenically unsaturated monomers, and physical blends of such homopolymers and copolymers together and/or with other polymers.

The Formula I $R_f$-monomers and polymers derived therefrom can be considered to be divided into two distinct classes due to their polymerization behavior.

These two classes are based on polymers derived from acrylates and methacrylates on one hand, as opposed to fumarates, maleates, mesaconates, citraconates, itaconates, and aconitates on the other hand. The latter class of esters tend to homopolymerize much less readily than the acrylates and methacrylates.

Turning to the first class which are acrylates and methacrylates, the polymerization will proceed as follows:

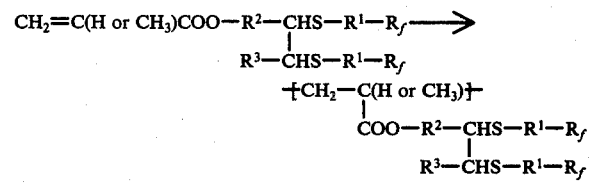

Formula I ⟶ Formula II

The acrylate and methacrylate monomers are highly reactive and have a great tendency to form homo- or copolymers. The polymer chain derived from Formula I acrylates or methacrylates will have two $R_f$ groups per monomer moiety.

The polymerization of the $R_f$-acrylate and $R_f$-methacrylate monomers is analogous to the polymerization of acrylate and methacrylate monomers, as described in Houben-Weyl, Methoden der Organischem Chemie, Vol. 14/1, p. 1044–1047, (Georg Thieme Verlag, Stuttgart, 1961) or C. E. Schildknecht, Vinyl and Related Polymers, p. 179–255 (John Wiley and Sons, Inc., New York 1952).

In contrast, the second group of polymers derived from $R_f$-fumarates, maleates, mesaconates, citraconates, itaconates and aconitates show a lower tendency toward hompolymerization and form low-molecular weight homopolymers, also called oligomers. They show however a great tendency to form alternating copolymers with certain types of comonomers as outlined later.

The polymer chain derived from $R_f$-fumarates and related di- and triesters contains four $R_f$-groups per monomer moiety as the following example shows:

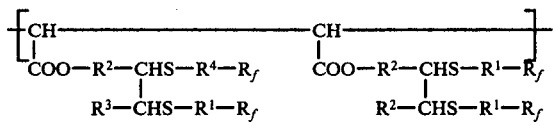

The polymerization of the $R_f$-fumarate and related di- and triester monomers of Formula I is analogous to the polymerization of alkyl fumarate or maleate monomers, as described in Houben-Weyl, Methoden der Organischem Chemie, Vol. 14/1 (Georg Thime Verlay Stuttgart, 1961) or C. E. Schildknecht, Vinyl and Related Polymers (John Wiley and Sons, Inc., New York, 1952).

The fact that in the novel polymers of Formula II the $R_f$-groups are present in closely packed clusters of 2 or more $R_f$-groups is most important, since the critical free surface energy of polymers with close-packed $R_f$-groups is lower and, consequently, the oil repellency is higher than in conventional $R_f$-polymers containing one $R_f$-group per backbone carbon or per monomer moiety.

Although the ease of polymerization will differ between the acrylate and methacrylate type monomers on one hand and the fumarate and related monomers on the other, similar conditions may be employed to obtain the desired polymerization.

Generally polymerization may be carried our in bulk, solution, suspension or emulsion. Solution and emulsion polymerizations are preferred.

In emulsion polymerization, the monomer or monomers to be polymerized are emulsified together in a water solution of a surface active agent to a given monomer concentration of from about 5% to about 50%. Usually the temperature is raised to between 40° C and 70° C to effect polymerization in the presence of an added catalyst. A suitable catalyst may be of any one of the commonly known agents for initiating the polymerization of an ethylenically unsaturated compound. The concentration of the catalyst for the polymerization is usually between 0.1% and 2% based upon the weight of the monomers.

Suitable surfactants or emulsifying agents include cationic, anionic or non-ionic types. Since the cationic and non-ionic types can be used in most textile treating baths, they are preferred. The hydrophobic portion of the surfactant may be hydrocarbon or fluorinated hydrocarbon.

Suitable surfactants or emulsifying agents include, for example, non-ionic surfactants in which the hydrophilic group is poly(ethoxy) group and the hydrophobic portion is either a hydrocarbon or a fluorocarbon group such as the ethylene oxide condensates of alkyl phenols, alkanols, alkylamines, alkyl thiols, alkylcarboxylic acids, fluoroalkyl carboxylic acids, fluoroalkyl amines and the like.

Suitable cationic surfactants include for example, quaternary ammonium salts or amine salts containing at least one long chain alkyl, fluoroalkyl, or high alkyl substituted benzene or naphthalene group to provide the hydrophobic portion.

Polymerization is preferably carried out for a reaction period adjusted to obtain essentially quantitative conversion of the fluorinated monomer. The optimum reaction time will depend upon the catalyst used and the polymerization temperature and other conditions, but will generally be in the range of from 0.5 to 24 hours.

The polymerization temperature will depend upon the catalyst chosen. In the case of emulsion polymerization in aqueous media, it will generally be in the range of from 20° C to 90° C. The polymerization is generally most conveniently and preferably carried out at atmospheric pressure wherever possible.

In solution polymerization, the monomer or monomers are dissolved in a suitable solvent such as fluorinated solvents, for example, hexafluoroxylene, trifluorotoluene or mixtures thereof with acetone and/or ethylacetate and polymerized in a reaction vessel using initiators such as azobisisobutyronitrile or other azo initiators at concentrations of 0.1 to 2.0% at 40°-100° C under nitrogen.

As mentioned, besides homopolymers, valuable copolymers are obtained by polymerization of the foregoing novel perfluorinated monomers with other polymerizable monomers having ethylene unsaturation.

The following types of comonomers are useful in the preparation of copolymers of the novel $R_f$-monomers:

Ethylene and chloro, fluoro- and cyano- derivatives of ethylene such as vinyl chloride, vinylidene chloride, vinyl fluoride, acrylonitrile, methacrylontrile, tetrafluoroethylene, hexafluoropropylene, acrylate and methacrylate monomers, particularly those with 1 to 12 or 18 carbon atoms in the ester groups such as n-propyl methacrylate, 2-methyl cyclohexyl methacrylate, methyl methacrylate, t-butyl methacrylate, n-butyl methacrylate, methyl acrylate, ethyl acrylate, propyl acrylate, butyl acrylate, 3-methyl-1pentyl acrylate, octyl acrylate, tetradecyl acrylate, s-butyl acrylate, 2-ethylhexyl acrylate, 2-methoxyethyl acrylate, and phenyl acrylate; dienes particularly 1,3-butadiene, isoprene, and chloroprene, 2-fluoro-butadiene, 1,1,3-trifluorobutadiene, 1,1,2,3-tetrafluoro butadiene, 1,1,2-trifluoro-3,4-dichlorobutadiene and tri- and pentafluoro butadiene and isoprene; nitrogenvinyl monomers such as vinyl pyridine, N-vinylamides, amides, vinyl succinimide, vinyl pyrrolidone, N-vinyl carbazole and the like; styrene and related monomers which copolymerize readily with the novel esters of this invention such as o-methylstyrene, p-methylstyrene, 3,4-dimethyl styrene, m-ethyl styrene, 2,5-diethyl styrene; vinyl esters, e.g. vinyl acetate, vinyl esters of substituted acids, such as for example, vinyl methoxyacetate, vinyl trimethylacetate, vinyl isobutyrate, isopropenyl butyrate, vinyl lactate, vinyl caprylate, vinyl pelargonate, vinyl myristate, vinyl oleate and vinyl linoleate; vinyl esters of aromatic acids, such as vinyl benzoate; alkyl vinylethers, such as methyl vinyl ether, isopropyl vinyl ether, isopropyl vinyl ether, isobutyl vinyl ether, 2-methoxy ethyl vinyl ether, n-propyl vinyl ether, t-butyl vinyl ether, isoamyl vinyl ether, n-hexyl vinyl ether, 2-ethylbutyl vinyl ether, diisopropylmethyl vinyl ether, 1-methyl-heptyl vinyl ether, n-decyl vinyl ether, n-tetradecyl vinyl ether, and n-octadecyl vinyl ether.

Propylene, butylene and iosbutylene are preferred α-olefins useful as comonomers with the novel fluoro monomers of the present invention with straight and branched chain α-olefins useful with up to 10 carbon atoms in the side chain.

Also useful as comonomers with some of the novel monomers of the present invention are vinyl monomers which contain perfluorinated side chains. Examples of such perfluorinated monomers are vinyl ethers of the type disclosed in U.S. Pat. No. 2,732,370, and U.S. Pat. No. 2,828,025; vinyl esters containing fluorinated alkyl groups disclosed in U.S. Pat. Nos. 2,592,069 and 2,436,144. Other useful monomers are acrylates and methacrylates and derivatives thereof such as those disclosed in U.S. Pat. Nos. 2,628,958; 3,256,230; 2,839,513; 3,282,905; 3,252,932; and 3,304,278.

Other $R_f$-group-containing monomers useful for copolymerization are fumarates, maleates, itaconates, and other $\alpha,\beta$-unsaturated di- and triesters as described in the following application and patents, assigned to the assignee of the instant invention: Ser. No. 720,370, filed Apr. 10, 1968, in the names of Eduard K. Kleiner and Martin Knell; U.S. Pat. No. 3,658,857, issued Apr. 25, 1972 in the names of Eduard K. Kleiner, Martin Knell and Pier Luigi Pacini, U.S. Pat. No. 3,636,085, issued Jan. 18, 1972 in the name of Eduard K. Kleiner, U.S. Pat. No. 3,658,843, issued Apr. 25, 1972 in the name of Eduard K. Kleiner, and U.S. Pat. No. 3,645,985, issued Feb. 29, 1972 in the name of Eduard K. Kleiner and Pier Luigi Pacini.

Of the listed comonomers, the acrylate and methacrylate monomers are the most important comonomers for the novel $R_f$-acrylates and $R_f$-methacrylates, whereas vinyl ethers, vinyl esters, styrenes and $\alpha$-olefins are the most important comonomers for the novel $R_f$-fumarates and related di- and triesters due to the fact that they form 1:1 alternating copolymers.

As mentioned, it may also be desirable to include a minor amount of other reactive comonomers in order to improve the wash and dry-clean properties of the novel textile finishes obtained according to the practice of this invention. Such monomers act as cross-linking agents during the curing operation. Such reactive comonomers are generally employed in amounts of 0.1% to 2%.

Reactive monomers which may be included are by way of illustration: acrylic acid, methacrylic acid, acrylamide, methacrylmiade, N-methylolacrylamide, 2-hydroxyethyl methacrylate or acrylate, hydroxypropyl acrylates or methacrylates, and t-butylaminoethyl methacrylate, and glycidyl methacrylate. Of the foregoing, N-methylolacrylamide and 2-hydroxyethyl methacrylate are preferred.

Coatings of the homopolymers and copolymers according to the instant invention can be prepared and applied from solvent solutions or from aqueous emulsions. Suitable solvents are fluoroalkanes, fluorochloroalkanes, fluoroalkyl substituted aromatics, alkyl esters or perfluoroalkanoic acids, chlorinated alkanes or aromatics, hydrocarbon aromatics, ketones, esters and ethers. Especially useful as solvents are the fluorinated liquids, and especially $\alpha,\alpha,\alpha$-trifulorotoluene, otherwise known as benzotrifluoride, hexafluoroxylene and mixtures of these with ethyl acetate or acetone and the like. Concentrations of the fluorinated polymers of the instant invention in solvent to provide coatings with effective oil and water repellency properties will generally be of the order of 0.01 to 10% and preferably from 0.1 to 2.0% by weight. Blends of the emulsions of the polymers of this invention with blended emulsions of other polymers and copolymers are particularly useful in textile finishes. The polymers and copolymers are generally of a non-fluorinated type; however, as indicated below other fluorinated polymers and copolymers may be used if desired. Nonfluorinated polymers useful in such blends, include for example, but without limitation, polymers and copolymers of alkyl acrylates and alkyl methacrylates, such as methyl methacrylate, ethyl methacrylate, hexyl methacrylate, and n-octyl methacrylate. A particularly suitable polymer is poly-n-octyl methacrylate. Also useful are polymers and copolymers of acrylic acid, methacrylic acid, styrene, alkyl styrene, butadiene, 2-methyl-1,3-butadiene, 2-chloro-1,3-butadiene; polymers and copolymers of vinyl esters such as vinyl acetate, vinyl butyrate, vinyl laurate, vinyl stearate, vinyl 2-ethyl-hexanoate; polymers and copolymers of vinyl halides and vinylidene halides, such as vinyl chloride, vinylidene chloride, vinyl fluoride, vinylidene fluoride; polymers and copolymers of allyl esters such as allyl propionate, or allyl caprylate; polymers and copolymers of vinyl ketones, such as vinyl methyl ketone, vinyl ethyl ketone, and the like; polymers and copolymers of vinyl ethers such as methyl vinyl ether, cetyl vinyl ether, and the like; polymers and copolymers of acrylamide, methacrylamide, N-methylol acrylamide, N-methylol methacrylamide, N-isopropyl acrylamide, and acrylonitrile and methacrylonitrile.

The polymers of this disclosure possess desirable soil repellency properties. A useful manner of measuring the relative ratings of the polymers is by oil and water repellency ratings. In the examples of the following test procedures were used:

The AATCC oil rating was determined according to Standard Test Method 118-1966 T of the American Association of Textile Chemists and Colorists. Ratings are given from 0 (minimum) to 8 (maximum). A commonly accepted level on soil repellent fabrics in the U.S. is an oil repellency of 4.

Another oil repellency method is the 3-M Oil Test procedure of Grajek and Peterson, Textile Research Journal, April 1962, p. 323.

The AATCC water spray test rating was determined according to Standard Test Method 22-1966 of the American Association of Textile Chemists and Colorists XXVII, 1961, P. 1952 (also designated ASTM-D-583-58). Ratings are given from 0 (minimum) to 100 (maximum).

The polymers in the examples were applied to polyester or polyester-cotton (65%/35%). The polymers were applied to yield a concentration of 0.08 and 0.12% fluorine based on the weight of the fabric.

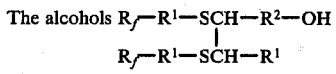

are prepared as disclosed in our copending application Ser. No. 652,367, filed Jan. 26, 1976. Specific examples of these alcohols are:

Structure

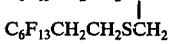

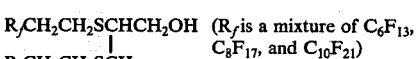
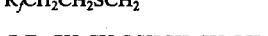

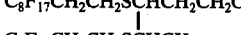
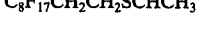

-continued

Structure (CF₃)₂CFOCF₂CF₂CH₂CH₂SCHCH₂OH
|
(CF₃)₂CFOCF₂CF₂CH₂CH₂SCH₂

C₈F₁₇CH₂SCHCH₂OH
|
C₈F₁₇CH₂SCH₂

C₈F₁₇(CH₂)₈SCHCH₂OH
|
C₈F₁₇(CH₂)₈SCH₂

C₈F₁₇CH₂CH₂SCHCH(OH)CH₃
|
C₈F₁₇CH₂CH₂SCHCH₂CH₃

C₈F₁₇CH₂CH₂SCHCH₂CH₂OH
|
C₈F₁₇CH₂CH₂SCH₂

C₈F₁₇CH₂CH₂SCH(CH₂)₄OH
|
C₈F₁₇CH₂CH₂SCH₂

C₈F₁₇CH₂CH₂SCH₂CH₂CH₂SCHCH₂OH
|
C₈F₁₇CH₂CH₂SCH₂CH₂CH₂SCH₂

C₈F₁₇CH₂CH₂OCH₂CH₂CH₂SCHCH₂OH
|
C₈F₁₇CH₂CH₂OCH₂CH₂CH₂SCH₂

C₈F₁₇CH₂CH₂N(CH₃)CH₂CH₂CH₂SCHCH₂OH
|
C₈F₁₇CH₂CH₂N(CH₃)CH₂CH₂CH₂SCH₂

To further illustrate the novel aspects of this invention relating to the novel α,β-unsaturated mono, di- and triesters of Formula I and the polymers of Formula II, the following Examples are provided. In the Examples, the temperatures are given in degrees centigrade unless otherwise indicated. Nuclear magnetic resonance data are given in parts per million, referred to the tetramethylsilane signal.

EXAMPLE 1

2,3-Bis(1,1,2,2-Tetrahydroperfluorodecylthio)propyl Methacrylate

CH₂=C(CH₃)
|
COOCH₂CHSCH₂CH₂C₈F₁₇
|
CH₂SCH₂CH₂C₈F₁₇

2,3-Bis(1,1,2,2-tetrahydroperfluorodecylthio)propan-1-ol(10.16g; 0.01 mole) was mixed in a 50 ml three neck flask with pyridine (0.83g; 0.01 mole) and 10 ml methyl ethyl ketone as solvent. The solution was warmed to 70° C under nitrogen and methacrylyl chloride (1.09g; 0.0105 mole) over 30 minutes. A white precipitate or pyridine hydrochloride formed, which was removed by filtration after a further hour at 70° C. The soild was washed two times with 5 ml. acetone and the washings and filtrate combined and stripped to an oil at 40° C and 15 mm. Hg. The product weighed 10.5g (96.8% of theory). Final purification was effected by passage through a short column of neutral alumina. Infrared showed bands at 1721 cm⁻¹ (C=O) and 1638cm⁻¹ (C=C). NMR showed signals at 1.92 ppm (3H) CH₂; 1.9-3.5 ppm (11H) CH + CH₂; 4.45 ppm (2H) OCH₂; 5.6 ppm (1H) = CH trans; 6.1 ppm (1H) = CH cis Elemental Analysis: Calc'd. for C₂₇H₁₈F₃₄O₂S₂: C: 29.90; H: 1.67; F: 59.56. Found: C: 30.31; H: 1.78; F: 59.04.

EXAMPLE 2

2,3-Bis(1,1,2,2-Tetrahydroperfluoroalkylthio)propyl Methacrylate

CH₂=C(CH₃)COOCH₂CHSCH₂CH₂R_f
|
CH₂SCH₂CH₂R_f (R_f = mixture of C₆F₁₃, C₈F₁₇ and C₁₀F₂₁ ratios as described) In a similar manner 2,3-bis(1,1,2,2-tetrahydroperfluoroalkylthio)propan-1-ol (50g; 0.0489 mole) (containing 4.0%, C₆C₆; 24.3% C₆C₈; 37.3% C₈C₈+C₆C₁₀; 25.5% C₈C₁₀; 6.4% C₁₀C₁₀ fluorinated chains) reacted with methacrylyl chloride (5.88g; 0.059 mole) and pyridine (4.91g; 0.059 mole) in benzene to give the mixed R_f-fumarate shown above. The product weighed 30.2g (59.8% of theory). Infrared showed C=O stretching frequency at 1720cm⁻¹ and C=C stretching frequency at 1637cm⁻¹. NMR showed signals at 1.95 ppm (3H) CH₃; 2.0-3.2 ppm (11H R_fCH₂CH₂ and SCHCH; 4.35 ppm (2H) OCH₂; 5.6 ppm (1H)=CH trans to C=O and 6.1 ppm (1H)=CH cis to C=O.

EXAMPLE 3

Bis[2,3-di(1,1,2,2-Tetrahydroperfluorodecylthio)propyl] Fumarate $$\left[ =CHCOOCH_2CHSCH_2CH_2C_8F_{17} \atop \phantom{=CHCOOCH_2}CH_2SCH_2CH_2C_8F_{17} \right]_2$$
trans 2,3-Bis(1,1,2,2-tetrahydroperfluorodecylthio)propan-1-ol (10.16g; 0.01 mole) was heated at 140° C, under nitrogen, with fumaryl chloride (0.76g; 0.005 mole) in 20 ml o-xylene. Upon cooling, a solid product separated. The curde produce was dissolved in 50 ml 1,1,1-trichloroethane and purified by passage through neutral alumina. Obtained 6.8g (64.4% of theory) m.p. 55°-60°. Infrared showed bands at 1721cm⁻¹ (C=O) and 1692cm⁻¹(C=C). NMR showed signals at 2.0-3.4 ppm (11H ) CH and CH₂; 4.43 ppm (4H) OCH₂; 6.85 ppm (2H)=CH Elemental Analysis: Calc'd. for C₅₀H₂₈F₆₈O₄S₄: C: 28.42; H: 1.34. Found: C: 28.79; H: 1.49.

EXAMPLE 4

Bis[2,3-di(1,1,2,2-Tetrahydroperfluoroalkylthio)propyl] Fumarate $$\left[ =CHCOOCH_2CHSCH_2CH_2R_f \atop \phantom{=CHCOOCH_2}CH_2SCH_2CH_2R_f \right]_2 \text{ trans}$$

Where R_f is as defined in Example 2. In a similar manner 2,3-bis(1,1,2,2-tetrahydroperfluoroalkylthio)-propan-1-ol (50g; 0.049 moles) was converted to 35.2g fumarate (67.7% yield) by reaction with fumaryl chloride (3.74g; 0.025 mole) in o-xylene at reflux temperature. The product was a tan, waxy solid, melting over the range 45°-55°.

Infrared showed C=O stretching frequency at 1722cm⁻¹ and C=C stretching frequency at 1694cm⁻¹.

EXAMPLE 5

Bis[2,3-di(1,1,2,2-Tetrahydroperfluorodecylthio)propyl] Itaconate

EXAMPLES 6-10

The scope of the invention is further illustrated by the following Examples of unsaturated esters prepared from $R_f$-alcohols by reaction with unsaturated acyl halides.

TABLE I

| Example | Alcohol or Diol | Acyl Halide | Product |
|---------|-----------------|-------------|---------|
| 6 | $C_8F_{17}CH_2CH_2SCHCH_2OH$<br>\|<br>$C_8F_{17}CH_2CH_2SCH_2$ | $CH_2=CHCOCl$ | $C_8F_{17}CH_2CH_2SCHCH_2OCOCH=CH_2$<br>\|<br>$C_8F_{17}CH_2CH_2SCH_2$ |
| 7 | $C_8F_{17}CH_2CH_2SCHCH_2OH$<br>\|<br>$C_8F_{17}CH_2CH_2SCHCH_3$ | $CH_2=C(CH_3)COCl$ | $C_8F_{17}CH_2CH_2SCHCH_2OCOC(CH_2)=CH_2$<br>\|<br>$C_8F_{17}CH_2CH_2SCHCH_2$ |
| 8 | $C_8F_{17}(CH_2)_8SCHCH_2OH$<br>\|<br>$C_8F_{17}(CH_2)_8SCH_2$ | $CH_2=CCOCl$<br>\|<br>$CH_2COCl$ | $C_8F_{17}(CH_2)_8SCHCH_2OCOC=CH_2$<br>\|     \|<br>$C_8F_{17}(CH_2)_8SCH_2$<br><br>$C_8F_{17}(CH_2)_8SCH_2$<br>\|<br>$C_8F_{17}(CH_2)_8SCHCH_2OCOCH_2$ |
| 9 | $C_8F_{17}CH_2CH_2SCH(CH_2)_4OH$<br>\|<br>$C_8F_{17}CH_2CH_2SCH_2$ | $CH_2=CCOCl$<br>\|<br>$CH_2COCl$ | $C_8F_{17}CH_2CH_2SCH(CH_2)_4OCOC=CH_2$<br>\|     \|<br>$C_8F_{17}CH_2CH_2SCH_2$<br><br>$C_8F_{17}CH_2CH_2SCH_2$<br>\|<br>$C_8F_{17}CH_2CH_2SCH(CH_2)_4OCOCH_2$ |
| 10 | $C_8F_{17}CH_2CH_2OCH_2CH_2CH_2SCHCH_2OH$<br>\|<br>$C_8F_{17}CH_2CH_2OCH_2CH_2CH_2SCH_2$ | $CH_2=CHCOCl$ | $C_8F_{17}CH_2CH_2OCH_2CH_2CH_2SCHCH_2OCOCH=CH_2$<br>\|<br>$C_8F_{17}CH_2CH_2OCH_2CH_2CH_2SCH_2$ |

$$CH_2=CCOOCH_2\overset{\overset{CH_2SCH_2CH_2C_8F_{17}}{|}}{C}HSCH_2CH_2C_8F_{17}$$
$$\overset{|}{CH_2COOCH_2\overset{\overset{}{|}}{C}HSCH_2CH_2C_8F_{17}}$$
$$\overset{|}{CH_2SCH_2CH_2C_8F_{17}}$$

2,3-Bis(1,1,2,2-tetrahydroperfluorodecylthio)propan-1-ol (10g; 0.098 mole) was mixed with pyridine (0.37g; 0.047 mole) in 20 ml of heptane, under nitrogen in a three-necked flask. Itaconyl chloride (0.78g; 0.047 mole) was added at 70° to the above mixture and the reaction was continued, with stirring for 17 hours. A small amount of black tarry material was removed by filtration and the curde product (8.7g; 87.4% of theory) was isolated by stripping off the heptane under reduced pressure. The itaconate was purified by passage through neutral alumina to obtain a product melting at 45°-55°. Infrared showed C=O stretching frequency at 1725cm$^{-1}$ and C=C stretching frequency at 1640cm$^{-1}$. NMR showed signals at: 2.0-3.3 ppm (22H) $C_8F_{17}CH_2Ch_2SCH$ and $C_8F_{17}CH_2CH_2SCH_2$; 3.4 ppm (2H)

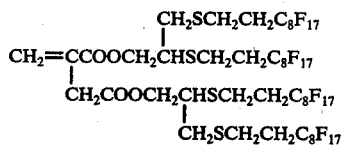

4.35 ppm (4H)

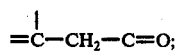

6.78 ppm (1H) trans to C=O and 6.38 ppm (1H) cis to C=O.

Elemental Analysis: Calc'd. for $C_{51}H_{30}F_{68}O_4S_4$: C: 28.80; I: 1.42; F: 60.74. Found: C: 28.90; I: 1.57; F: 59.30.

EXAMPLE 11

Bis[2,3-di(1,1,2,2-Tetrahydroperfluoroalkylthio)propyl] with Vinyl Acetate

Bis[2,3-di(1,1,2,2-Tetrahydroperfluoroalkylthio)-propyl]fumarate (4.0g; 0.019 mole), vinyl acetate (0.16g; 0.0019 mole), azobisisobutyronitrile (0.02g) and 4g hexafluoroxylene were sealed in an ampoule under nitrogen and heated for 16 hours at 80° C. The solution then was diluted with 8g hexafluoroxylene and poured into 240 ml methanol. The precipitated polymer was filtered, washed and vaccum dried, yielding 2.44g (58.6% yield) of a pale beige powder.

Elemental Analysis: Calc'd. C: 29.49; H: 1.56; F: 58.75. Found: C: 28.89; H: 1.33; F: 60.21.

EXAMPLE 12

Fumarate Copolymer with Styrene

Using the fumarate of Example 11 and the method described in Example 11, the fumarate was heated with styrene (0.20g; 0.0019 mole). Work up gave 2.79g (66.6% yield) of a pale beige powder.

Elemental Analysis: Calc'd. C: 31.42; H: 1.64; F: 58.27. Found: C: 31.12; H: 1.51; F: 58.40.

EXAMPLE 13

Copolymer of the Fumarate with Vinyl Methyl Ether

Following the procedure of Example 11, the polymerization was carried out with vinyl ether (0.11g; 0.019 mole). Work up gave 1.89g (46.2% yield) of a pale beige powder.

Elemental Analysis: Calc'd. C: 29.32; H: 1.58; F: 59.51. Found: C: 29.14; H: 1.41; F: 60.14.

EXAMPLE 14

Copolymer of the Fumarate with Vinyl Pyrrolidone

Following the procedure of Example 11, the polymerization was carried out with vinyl pyrrolidone (0.21g; 0.0019 mole). Work up gave 2.74g (65.1% yield) of a pale beige powder.

Elemental Analysis: Calc'd. C: 30.24; H: 1.68; F: 58.09; N: 0.63. Found: C: 29.35; H: 1.69; F: 59.56; N: 0.72.

EXAMPLE 15

Homopolymerization of Bis[2,3-di-(1,1,2,2-Tetrahydroperfluoroalkylthio)-propyl]Fumarate Bis[2,3-di(1,1,2,2-tetrahydroperfluoroalkylthio)-propyl]fumarate (4.00g; 0.0019 mole) and benzoyl peroxide (0.01g) were sealed in an ampoule under nitrogen and heated at 80° C for 16 hours. The solid polymer was washed with 8 ml acetone, then dissolved in 12g hexafluoroxylene and finally recovered by precipitation in 240 ml methanol. Filtration and drying gave 2.14g (53.5% yield) of polymer.

Elemental Analysis: Calc'd. C: 28.42; H: 1.34; F: 61.15. Found: C: 27.91; H: 1.19; F: 61.66.

EXAMPLE 16

Copolymer of Bis[2,3-di(1,1,2,2-Tetrahydroperfluorodecylthio)-propyl]Fumarate and Vinyl-2-Methoxyethylether Bis[2,3-di(1,1,2,2-tetrahydroperfluorodecylthio)-propyl]fumarate (1.90g; 0.0009 mole), vinyl-2-methoxyethyl ether (0.092g; 0.0009 mole) and azobisisobutyronitrile (0.01g) were added to 2g hexafluoroxylene and sealed under nitrogen in an ampoule. The solution was heated at 80° C for 16½ hours, then diluted with a further 4g hexafluoroxylene. The polymer was precipitated by pouring the solution into some methanol. Filtration and drying gave 1.41g (71% yield) of an off-white powder.

Elemental Analysis: Calc'd. C: 29.82; H: 1.73; F: 59.33. Found: C: 29.47; H: 1.43; F: 60.82.

EXAMPLE 17

Copolymer of Example 16 Fumarate with Styrene

Following the procedure of Example 16, the polymerization was carried out with styrene (0.094g; 0.0009 mole). The product was isolated in the manner described, yielding 1.37g (68% yield) of an off-white powder.

Elemental Analysis: Calc'd. C: 31.42; H: 1.64; F: 58.27. Found: C: 31.38; H: 1.73; F: 58.18.

EXAMPLE 18

Homopolymer of 2,3-Bis(1,1,2,2-Tetrahydroperfluorodecylthio)Propyl Methacrylate 2,3-Bis(1,1,2,2-tetrahydroperfluorodecylthio)propyl methacrylate (2.00g), dodecyl mercaptan (0.1g) and azobisisobutyrinitrile (0.1g) were added to 10g hexafluoroxylene and sealed under nitrogen in an ampoule. The solution was heated at 80° C for 17 hours, then diluted with a further 4g hexafluoroxylene and then poured into 120 ml methanol. The precipitated polymer was washed and dried to give 1.69g 80% yield) of a brittle, beige solid.

Elemental Analysis: Calc'd. F: 54.02. Found: F: 54.19.

EXAMPLE 19

The utility of the polymers of the preceding Examples is illustrated in Table II. The materials were applied to the indicated fabrics at a loading of 0.12% fluorine on the treated fabric and tested for oil and water repellency by the methods already described.

TABLE II

| Fluoropolymer Example | Polyester Double Knit | | | 65/35 Polyester/Cotton | | | 100% Cotton Print | | | 100% Wool | | |
|---|---|---|---|---|---|---|---|---|---|---|---|---|
| | Oil $A^2$ | Rep. 3M | Water Rep. $A^2$ | Oil $A^2$ | Rep. 3M | Water Rep. $A^2$ | Oil $A^2$ | Rep. 3M | Water Rep. $A^2$ | Oil $A^2$ | Rep. 3M | Water Rep. $A^2$ |
| 11 | 6 | 110 | 80 | | | | | | | | | |
| 12 | 6 | 110 | 90 | 5 | 100 | 70 | 5 | 100 | 50 | 8 | 140 | 100 |
| 13 | 6 | 120 | 100 | | | | | | | | | |
| 14 | 6 | 120 | 100 | 5 | 110 | 50 | 5 | 90 | 50 | 8 | 140 | 100 |
| 15 | 6 | 110 | 80 | | | | | | | | | |
| 16 | 6 | 110 | 90 | | | | | | | | | |
| 17 | 6 | 120 | 100 | | | | | | | | | |
| 18 | 3 | 80 | 90 | | | | | | | | | |

$A^2$ = AATCC oil rating or water spray test rating
3M = 3M Oil Test

What is claimed is:

1. A compound of the structure $$R^4\diagdown_{\phantom{C}}\diagup R^6$$
$$C=C$$
$$R^5\diagup \phantom{C}\diagdown COO-R^2CHS-R^1R_f$$
$$\phantom{R^5\diagup COO-R^2C}|$$
$$\phantom{R^5\diagup COO-}R^3-CHS-R^1R_f$$

wherein
R$^1$, R$^2$ are each C$_n$H$_{2n}$, where $n$ is 1 to 12 and may be straight chain or branched;
R$^3$ is hydrogen or C$_n$H$_{2n+1}$, where $n$ is 1 to 12 and may be straight chain or branched;
R$^4$, R$^5$ and R$^6$ are hydrogen, methyl $$-COO-R^2-CHS-R^1-R_f$$
$$|$$
$$R^3-CHS-R^1-R_f,$$
or
$$-CH_2COO-R^2-CHS-R^1-R_f$$
$$|$$
$$R^3-CHS-R^1-R_f,$$

provided that at least one of R$^4$, R$^5$ and R$^6$ is hydrogen or methyl;
R$_f$ is C$_p$F$_{2p+1}$ or C$_p$F$_{2p+1}$OC$_q$F$_{2q}$, where $p$ is 3 to 18, $q$ is 2 to 8.

2. A compound of claim 1, wherein R$^4$, R$^5$ and R$^6$ are hydrogen or methyl.

3. A compound of claim 2, wherein at least two of $R^4$, $R^5$ and $R^6$ are hydrogen.

4. A compound of claim 1, wherein one of $R^4$, $R^5$ and $R^6$ is $$-COO-R^2-\underset{\underset{R^3-CHS-R^1-R_f}{|}}{CHS}-R^1-R_f \quad \text{or} \quad -CH_2COO-R^2-\underset{\underset{R^3-CHS-R^1-R_f}{|}}{CHS}-R^1-R_f.$$

5. A compound of claim 1, wherein $R_f$ is a straight-chain group of formula $C_pF_{2p+1}$, where $p$ is 6 to 12.

6. A compound of claim 1, wherein
$R^1$ is $-CH_2CH_2-$
$R^2$ is $-CH_2-$, and
$R^3$ is hydrogen.

7. A compound of claim 2, wherein $R_f$ is a straight-chain group of formula $C_pF_{2p+1}$, where $p$ is 6 to 12.

8. A compound of claim 7, wherein
$R^1$ is $-CH_2CH_2-$
$R^2$ is $-CH_2-$, and
$R^3$ is hydrogen.

9. A compound of claim 6, wherein $R^4$ and $R^5$ are hydrogen, $R^6$ is methyl and $R_f$ is $C_6F_{13}$, $C_8F_{17}$, $C_{10}F_{21}$ or a mixture thereof.

10. A compound of claim 9, wherein $R_f$ is $C_8F_{17}$.

11. A compound of claim 6, wherein $R^4$ is $$-CH_2COOCH_2-\underset{\underset{CH_2SCH_2CH_2R_f}{|}}{CHSCH_2CH_2R_f};$$

$R^5$ and $R^6$ are hydrogen: and $R_f$ is $C_6F_{13}$, $C_8F_{17}$, $C_{10}F_{21}$ or a mixture thereof.

12. A compound of claim 11, wherein $R_f$ is $C_8F_{17}$.

13. A compound of claim 6, wherein $R^4$ and $R^5$ are hydrogen, and $$R^6 \text{ is } CH_2COOCH_2\underset{\underset{CH_2SCH_2CH_2R_f}{|}}{CHSCH_2CH_2R_f}$$

where $R_f$ is $C_6F_{13}$, $C_8F_{17}$, $C_{10}F_{21}$ or a mixture thereof.

14. A compound of claim 13, wherein $R_f$ is $C_8F_{17}$.

* * * * *